United States Patent [19]

Ansite

[11] Patent Number: 4,506,667
[45] Date of Patent: Mar. 26, 1985

[54] SELF-CONTAINED VENTILATOR/RESUSCITATOR

[76] Inventor: William K. Ansite, 1212 N. Jackson St., Glendale, Calif. 91207

[21] Appl. No.: 482,621

[22] Filed: Apr. 6, 1983

[51] Int. Cl.³ .................................. A62B 7/10
[52] U.S. Cl. ...................... 128/204.25; 128/202.26; 128/205.12; 128/205.16; 128/201.25
[58] Field of Search ............ 128/204.25, 202.26, 128/204.24, 204.26, 204.28, 205.11, 205.12, 205.13, 205.14, 205.15, 205.16, 205.17, 205.18, 205.22, 205.24, 201.25

[56] References Cited

U.S. PATENT DOCUMENTS

| | | | |
|---|---|---|---|
| 1,005,816 | 10/1911 | Drager. | |
| 2,325,049 | 7/1943 | Frye et al. | 128/204.25 |
| 2,428,451 | 10/1947 | Emerson | 128/29 |
| 2,737,177 | 3/1956 | Anklin | 128/29 |
| 2,896,617 | 7/1959 | Gibbons | 128/201.23 |
| 3,046,979 | 7/1962 | Andreasen | 128/29 |
| 3,200,816 | 8/1965 | Bartlet, Jr. | 128/142 |
| 3,863,630 | 2/1975 | Cavallo | 128/204.21 |
| 3,971,372 | 7/1976 | Lenk et al. | 128/142 R |
| 3,974,828 | 8/1976 | Bird | 128/204.25 |
| 4,164,218 | 8/1979 | Martin | 128/142.7 |
| 4,314,566 | 2/1982 | Kiwak | 128/204.15 |
| 4,331,141 | 5/1982 | Pokhis | 128/202.27 |
| 4,351,329 | 6/1982 | Ellested et al. | 128/204.21 |

FOREIGN PATENT DOCUMENTS

| | | | |
|---|---|---|---|
| 16792 | 9/1955 | Fed. Rep. of Germany | 128/204.25 |
| 13805 | 7/1956 | Fed. Rep. of Germany | 128/204.25 |
| 1931816 | 6/1971 | Fed. Rep. of Germany | 128/205.16 |
| 818839 | 6/1937 | France | 128/205.12 |

OTHER PUBLICATIONS

Scott Emergency Escape Breathing Device, Scott Aviation—Lancaster, New York.
Scott Aviox Portable Oxygen Breathing Units, Scott Aviation—Lancaster, New York.

Primary Examiner—Henry J. Recla

[57] ABSTRACT

A self-contained portable ventilator/resuscitator which can be operated from either an internal power source, or in the event that the power source fails, can be manually operated to provide the patient with a supply of filtered ambient gases. The ventilator/resuscitator includes a housing (12) in which is mounted a chlorate candle (36), a filter (38), a pump (32), and control means (34). The pump is caused to be operated by the chlorate candle and will cause ambient gases to be drawn into the filter to be mixed with the output of the candle for subsequent delivery to the patient. The device further includes an accumulator (14) which, during normal operation, stores excess gases during the expiratory cycle, and, in the event that the chlorate candle ceases operation, can be manually operated through movement of the handle (90) to either draw gases into the accumulator through filter (38) or to force the filtered gases into the lungs of the patient.

10 Claims, 3 Drawing Figures

SELF-CONTAINED VENTILATOR/RESUSCITATOR

FIELD OF THE INVENTION

The present invention relates generally to a respiratory device, and more particularly to a self-contained portable ventilator/resuscitator provided with an internal power supply and power operated pump and control means which, in normal operation operates cyclically to force filtered air and oxygen into the lungs of the patient and then to permit the patient's respiratory cavity to expire, said ventilator/resuscitator also capable of being operated manually if the power supply should fail.

BACKGROUND OF THE INVENTION

Various types of respiratory devices are well known in the art, and the present invention deals with that class of devices generally referred to as either resuscitators and/or ventilators, depending upon the primary intended usage. One prior art device is a "Bear II Ventilator". In one mode of operation the ventilator forces a tidal volume of an air oxygen mixture into a patient's lungs for a prescribed period of time, for example two seconds, and then permits the patient's respiratory cavity to collapse thereby expelling the air oxygen mixture for another prescribed period of time, for example four seconds. This same ventilator may also be operated in another mode wherein, in addition to operating in a timed cycle, it would also sense through pressure changes spontaneous inspiratory effort by the patient, which sensed changes would cause the ventilator to switch from expiratory mode to an inspiratory mode. Thus, if the ventilator were in the expiratory mode, and the patient desired to inhale, electronic circuitry could cause the device to shift into its inspiratory mode.

While devices similar to the "Bear" unit are for hospital use, it is desirable that a lightweight portable ventilator/resuscitator be developed which is capable of utilizing filtered ambient gases, to supplement an internal source of pressurized breathing gases, the ambient gases passing through a filter to remove toxic or harmful contaminants. Such a device would find utility with the Armed Forces, for example where servicemen may be subjected to nerve gas attacks. Such a portable ventilator/resuscitator should initially operate from an internal power supply, such as the source of pressurized breathing gases (which may be an oxygen generator or a container of compressed gas), but it is desirable that upon failure of the internal power supply that it can also be operated in a manual mode.

OBJECTS AND SUMMARY OF THE INVENTION

It is an object of the present invention to provide a self-contained portable ventilator/resuscitator capable during normal operation of supplementing an internal gas supply with filtered ambient gases and cyclically forcing such gases into the lungs of the patient and then permitting the patient's respiratory cavity to expire, which self-contained portable ventilator/resuscitator can be manually operated when it ceases to operate in its normal mode.

More specifically, it is an object of the present invention to provide a self-contained portable ventilator/resuscitator of the type having a filter capable of filtering ambient gases, pump means normally operable to cause ambient gases to be drawn through said filter, control means capable of either directing the output of the pump to an outlet to a patient during an inspiratory mode of operation, or directing the output of the pump to an accumulator during an expiratory mode, and means capable of manually expanding and retracting the accumulator and operable, when the pump fails to operate normally, to draw ambient gases through the filter and into the accumulator when the accumulator is being manually expanded, and to force the filtered gases into the patient when the accumulator is being manually retracted.

It is an additional object of the present invention to provide the apparatus as set forth in the preceding paragraph wherein the pump and/or the control means is powered by a source of pressurized breathing gas, such as oxygen, which is part of the self-contained portable ventilator/resuscitator, the filtered ambient air being mixed with the oxygen.

It is an additional object to provide a ventilator/resuscitator of the type referred to above which may be readily secured to the clothing of a patient.

The foregoing objects, as well as other objects and advantages of this invention are accomplished by providing a self-contained portable ventilator/resuscitator assembly including a housing which receives side by side cylindrical members, one of which contains a source of pressurized breathing gases, and the other being a filter having an inlet end open to ambient gases. The housing further contains a jet pump, the nozzle of which is connected to the source of pressurized breathing gases, and the suction side of the jet pump being connected to the outlet end of the filter. The housing is also provided with control means which may include fluidic elements, air logic elements, or both, the operation of which is preferably powered by the source of pressurized breathing gases. Mounted on one end of the housing is a bellows-type accumulator having a rigid end wall spaced away from the housing, a handle in the form of a bent outlet pipe being secured to the end wall, and the bent outlet pipe also being connected to an extensible and retractable outlet connection disposed within the accumulator. During normal operation pressurized breathing gases are mixed with filtered ambient gases within the pump, the mixed gases being cyclically directed either to the patient or to the accumulator during inspiratory and expiratory modes, respectively. After the source of pressurized breathing gases is depleted the accumulator can be manually operated to either draw filtered ambient gases into the accumulator as the accumulator is expanded, or alternatively to force filtered ambient air into the lungs of the patient as the accumulator is retracted.

The above and additional details are more fully set forth in the following detailed description and the accompanying drawings.

DETAILED DESCRIPTION OF A PREFERRED EMBODIMENT

Figure 1:
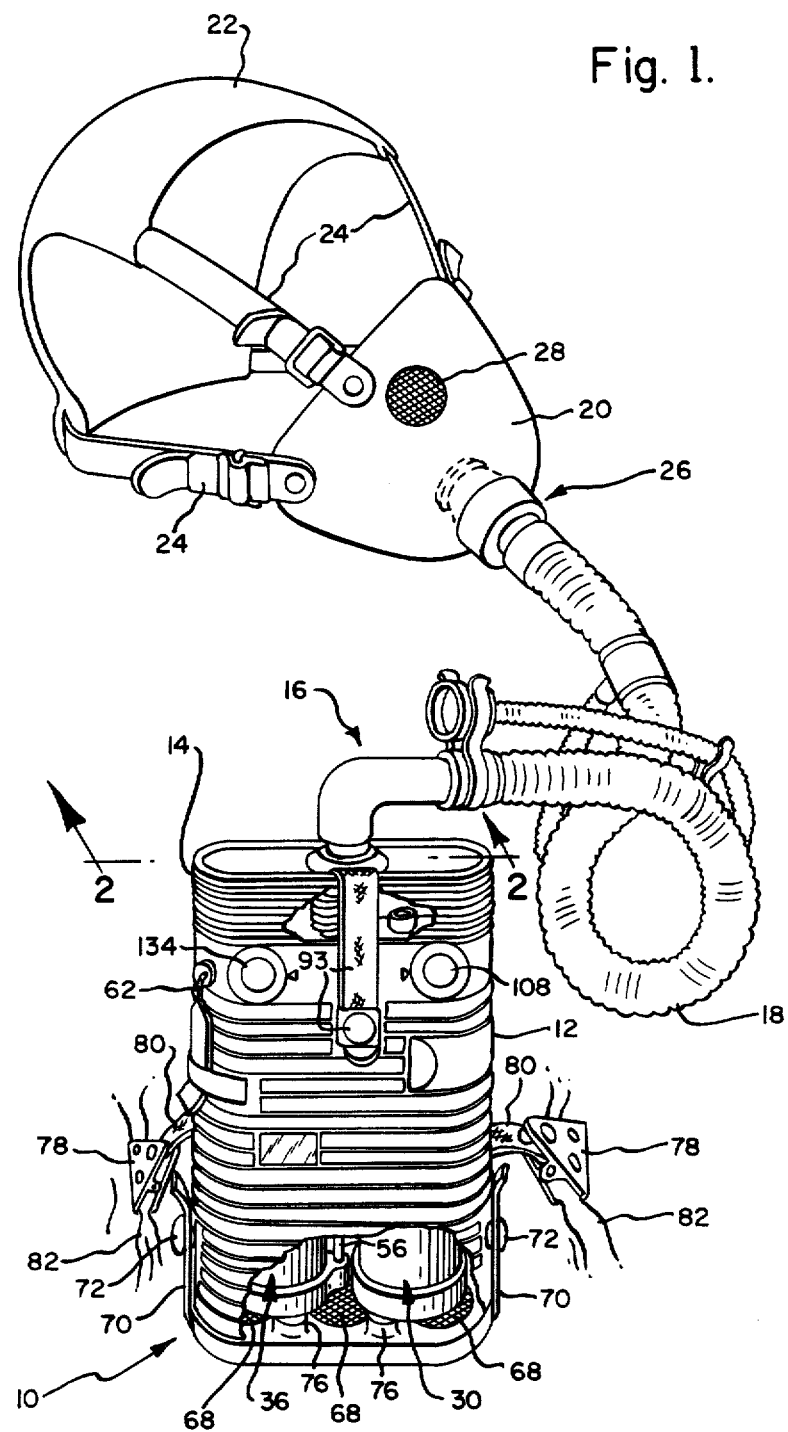
FIG. 1 is an overall view of the self-contained portable ventilator/resuscitator of this invention.
Figure 2:
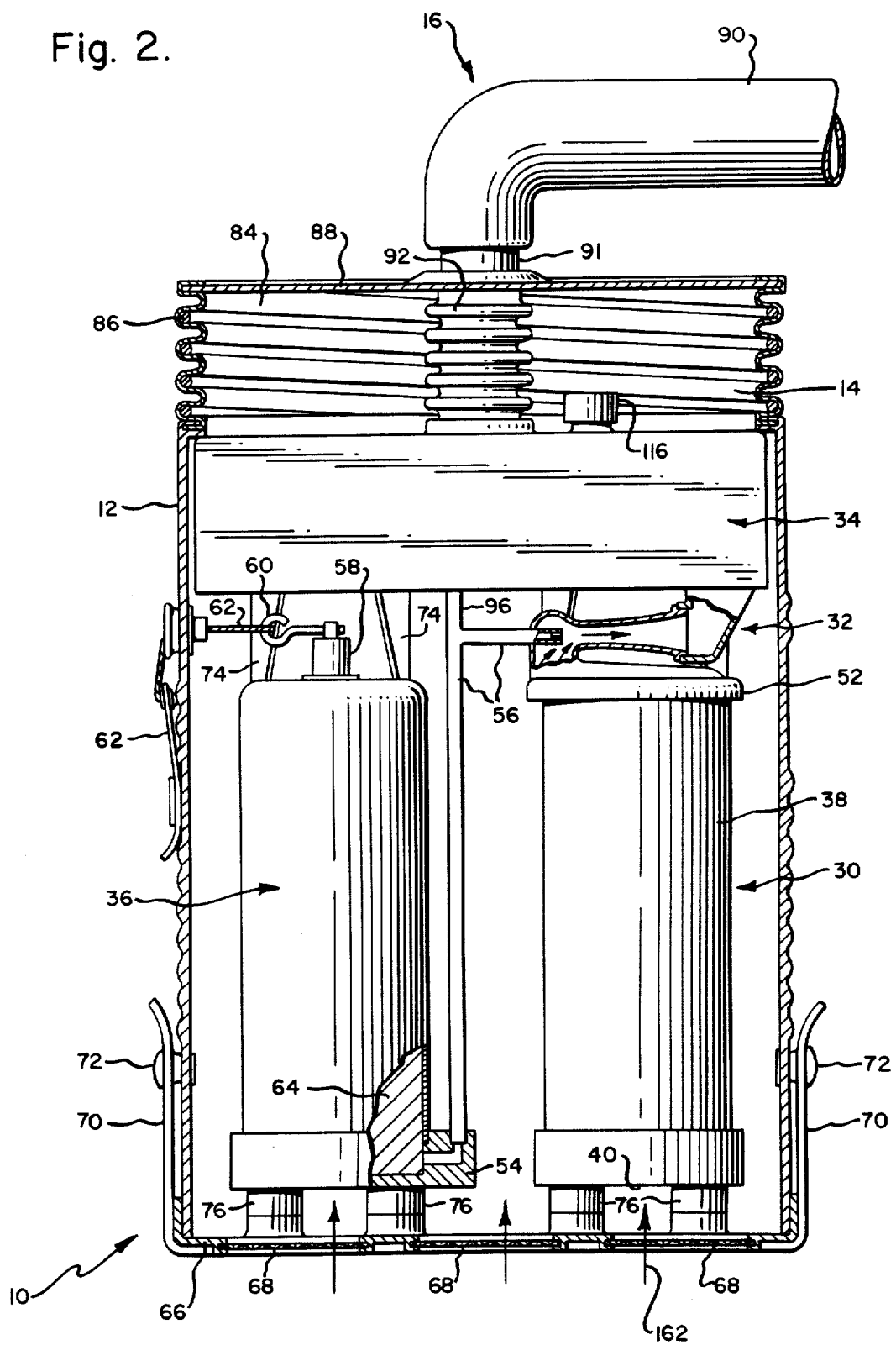
FIG. 2 is a sectional view taken generally along the line 2—2 in FIG. 1 showing further details of various elements of the ventilator/resuscitator.

The ventilator/resuscitator of the present invention in indicated generally at 10 in FIGS. 1 and 2 and includes a relatively rigid case or housing 12 within which various of the operational components of the ventilator/resuscitator may be housed. Mounted on one end of the housing 12 is a bellows-type accumulator 14. Passing through the accumulator 14 is an outlet indicated generally at 16.

In addition to the housing 12 and accumulator 14 the ventilator/resuscitator is also provided with a mask, harness, and suitable tubing, for interconnecting the outlet 16 with the patient. This structure forms no part of the present invention and is covered by a copending patent application. However, it should be noted that flexible tubing 18 is secured at one end to the outlet 16 and is secured at the other end to a mask 20. The mask 20 is adapted to be held over the nose and mouth of a patient by means of a harness 22 and adjustable straps 24. The mask 20 may be provided with an inhalation-/exhalation valve assembly indicated generally at 26 and an anti-suffocation valve indicated at 28.

Mounted within the housing 12 is a filter indicated generally at 30, pump means indicated generally at 32, control means indicated generally at 34, and a source of pressurized breathing gas indicated generally at 36.

The filter 30 includes a generally cylindrical container 38 in which suitable filtering material, such as activated charcoal, is mounted. As viewed in FIG. 2 the upper end wall of the generally cylindrical filter is the outlet and the lower end wall 40 is the inlet.

Disposed immediately above the outlet end of the filter 30 and below the controls 34 is the pump 32. The pump is in the form of a jet pump, the jet pump including a nozzle 42 (best shown in FIG. 3.), a body 44 including a diffuser 46, a suction portion 48, and a discharge portion 50. The suction portion 48 includes a cylindrical part 52 which can receive the upper end of the container 38 in a gas tight relationship. The various parts of the pump 32 are secured to the housing 12 in a manner not material to the present invention.

While the source of pressurized breathing gas 36 could be a container of oxygen under pressure, it is preferably in the form of a chlorate candle. Such a candle is customarily provided with a discharge opening 54 which can in turn be interconnected with tubing means 56 which in this case would be interconnected with the nozzle 42 of the jet pump. The operation of the chlorate candle is initiated by a primer indicated at 58, the operation of which is in turn initiated by pulling pin 60 by means of a lanyard 62. Once the operation of the candle has been initiated it will burn, forcing oxygen through a filter bed 64 and through the discharge opening 54 and on to the jet pump. The chlorate candle 36 is in the form of a cylindrical element.

In order to provide for the assembly and removal of both the filter 30 and the chlorate candle 36 the housing 12 is provided with a removable bottom element 66, which element is relatively rigid and provided with screened apertures 68 in its bottom. The bottom element is secured in place by straps 70 and fasteners 72. Internally, the housing is provided with depending support elements 74 which are adapted to contact the top of the candle 36 to limit its upper movement and in a similar manner the cylindrical part 52 limits the upward movement of the filter 30. The filter 30 and the candle 36 are held against the support elements 74 and the cylindrical part 52 by means of abutments 76 carried by the bottom element 66.

As can best be seen in FIG. 1 clothes clips 78 are provided, which clothes clips are secured to the housing 12 by means of flexible straps 80, and which can in turn be secured to the clothing (illustrated in part at 82) of a patient.

The accumulator 14 is of a bellows type and is provided with a pleated or convoluted sidewall of flexible impervious material, which sidewall is normally spring biased to its normal retracted position by an internal spring 86. (In the alternative, this could be accomplished by the set of the pleated sidewall itself.) One end of the accumulator is provided with a rigid end wall 88 which is spaced away from the housing 12. This end wall can be moved towards or away from the housing by manual operation and to this end the outlet 16 includes a right angle tube 90 and nipple 91 which are rigidly secured to each other and to the end wall 38 by welding or the like. Thus this tube serves as a handle which can be engaged manually to pull the end plate away from the housing 12 to expand the accumulator, or, in the alternative, it can be forced towards the housing 12 to retract the accumulator. The nipple 91 is further operatively connected to an extensible and retractable tube 92 disposed within the accumulator, the last mentioned tube also forming part of the outlet to the patient. Before use, the accumulator is held in its retracted position by strap and fastener 93.

Figure 3:
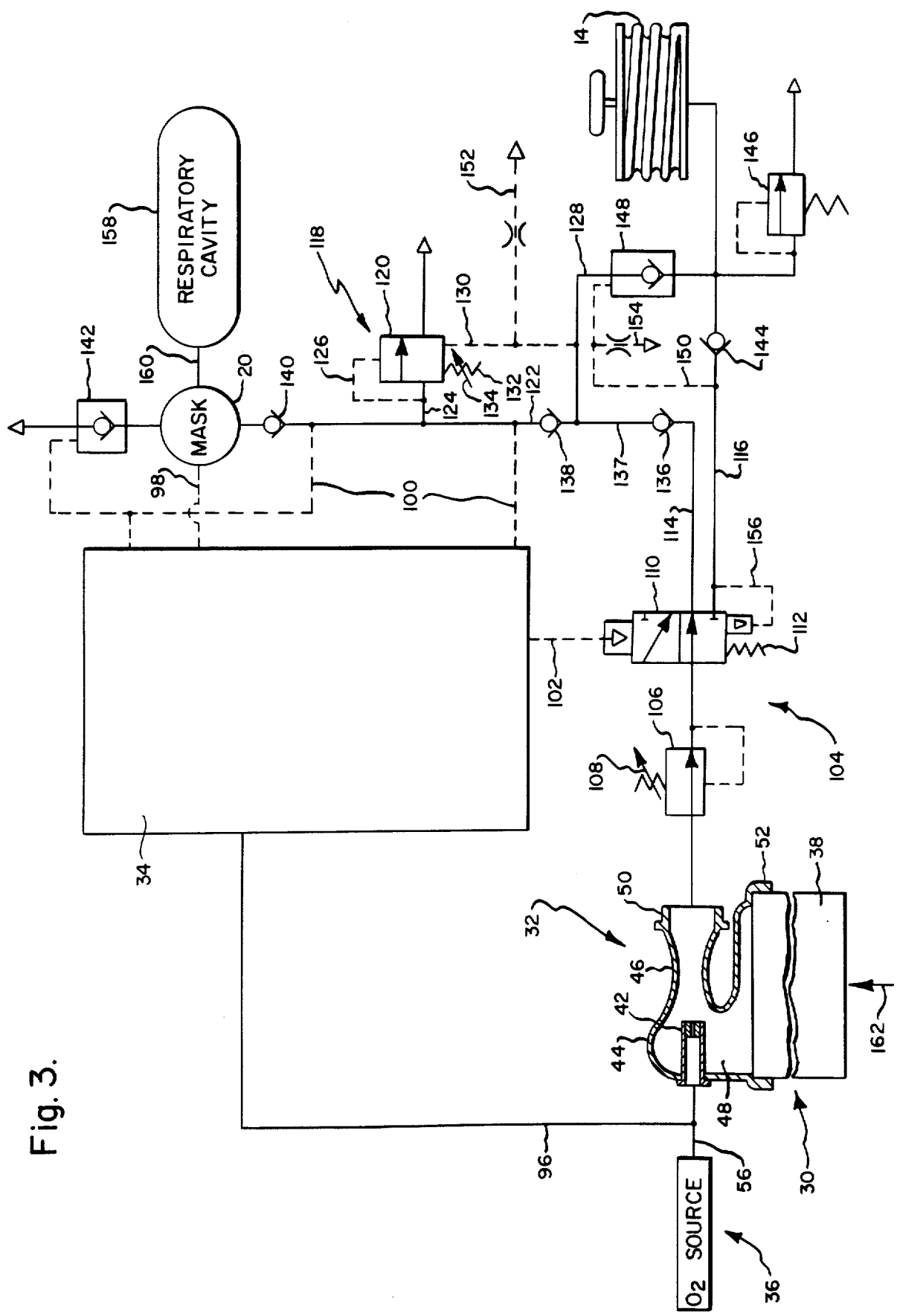
FIG. 3 is a schematic illustration of various operational components of the ventilator/resuscitator.

As previously indicated the control means 34 is contained within the canister housing 12 at the upper end thereof. However, the control means 34 may include elements external of the housing 12, such as the outlet 16, flexible tubing 18, and the inhalation/exhalation valve assembly 26 which has been previously referred to. The inhalation/exhalation valve 26 assembly may be of the type shown in U.S. Pat. No. 3,342,200, or alternatively, it may be formed of separate components as indicated in FIG. 3. While the form generally shown in U.S. Pat. No. 3,342,200 is preferred, it will be described as separate components for the sake of convenience to the understanding of the nature of this invention.

The control means 34 includes a primary control unit indicated generally at 94, which control unit is capable of directing the output of the pump to the patient during a timed inspiratory phase, or to the accumulator during a timed expiratory phase, which primary control unit is also pressure responsive to either inspiratory or expiratory effort on the part of the patient to override the timed functions. Such a primary control unit may be of the type shown in applicant's copending U.S. application Ser. No. 459,405 filed Jan. 20, 1983. The primary control unit includes fluidic and/or air logic control and timing units and is powered by means of pressurized breathing gas received from branch line 96. The primary unit is connected to various pressure sensing lines 98, 100 which either sense the pressure in the outlet 16 and/or mask 20, and it is further provided with an outlet control line 102 the purpose of which will be described later.

In addition to the primary control unit 94, the control means 34 includes various control valves indicated generally at 104. Thus, immediately downstream of the discharge portion 50 of the jet pump 32 is a pressure or flow regulating valve indicated at 106 for insuring that a relatively constant output is provided to the system. The output of this valve can be varied by a control knob indicated at 108 in FIG. 1 and by the arrow in FIG. 3. Downstream of the valve 106 is a distributor valve 110 the operation of which is normally controlled by the primary control unit 94 through output control line 102. Thus, the valve 110 is normally spring biased to its inspiratory position illustrated in FIG. 3 by spring 112 but may be shifted to its expiratory position in response to control pressure in line 102. When the valve is in the inspiratory position the output of the pump will be directed initially into line 114 and when in the expiratory position pump output will be directed initially into line 116 which terminates within the accumulator as can be seen in FIG. 2. The control valves further include a PEEP (positive end expiratory pressure) valve which is indicated generally at 118, the PEEP valve including a pressure compensated relief valve 120 which is connected to output line 122 by a further line 124 and pilot line 126 and to branch line 128 by pilot line 130. The pressure relief valve 120 is, as customary, normally biased to a blocking position by a spring 132, the pressure of which can be varied by a control knob indicated at 134 in FIG. 1 and by the arrow in FIG. 3. A first check valve 136 is disposed between line 114 and line 137 which connects to the branch line 128, and a second check valve 138 is disposed between line 137 and line 122. The output line 122 beyond the PEEP valve 118 is interconnected with the extensible end cavity will contract forcing air from the lungs into the mask and thence through the pressure compensated check valve 142 to atmosphere. The normal inspiratory/expiratory cycle will be initiated by an operator initiating the operation of the chlorate candle by pulling the lanyard 62 which will in turn cause the primer 58 to fire. Oxygen will now be delivered through tubing 56 to the jet pump 32 and also through line 96 to the primary control 94. The primary control 94 will cause the distributor valve 110 to shift between inspiratory and expiratory positions in response to either a timed cycle or in response to inspiratory or expiratory efforts on the part of the patient. In addition, ambient gases will be drawn up through the filter 38 in a direction indicated by the arrow 162. The operator can adjust the volume of air to be used in each cycle of operation by means of the control knob 108, and in addition may adjust the positive end expiratory pressure by means of control knob 134.

When the valve 110 is in the inspiratory position as illustrated in FIG. 3 pressurized breathing gases during normal operation will flow from the pump 32 through valve 110 and into line 114 past check valve 136, line 137, check valve 138, line 122 and finally to the mask 20 past check valve 140. During the initial inspiratory cycle flow through branch line 128 will be blocked by check valve 148 and the pressure compensated relief valve will be retractable tube 92, nipple 91, the right angle tube 90, and the flexible tubing 18 and is provided with a pressure compensated inhalation/exhalation valve (such as 26) which includes a check valve 140 and pressure compensated check valve 142 which is capable of sensing pressure in the output line 122 or 16 through pressure sensing line 100.

The line 116 extends to the accumulator 14 through a check valve 144, there being a pressure relief valve 146 in communication with the line 116 downstream of the check valve 144. When the accumulator is discharging its output will be routed through a pressure compensated check valve 148 and into branch line 128. The pressure compensated check valve 148 is compensated by means of pilot line 150 which is connected at one end to line 116 above the check valve 144. Both the pilot line 130 and the pilot line 150 are provided with separate bleed to atmosphere lines 152, 154, respectively. Finallly, the control means also includes a pilot line 156 which is capable of causing the distributor valve 110 to be shifted from its normal inspiratory position to its expiratory position in the event that the pressure in line 116 drops below atmosphere.

In operation, the ventilator/resuscitator will be used by initially placing the mask 20 over the nose and mouth of a patient, the mask being secured in place by harness 22 and straps 24. The patient is in part indicated by the respiratory cavity 158 and breathing gases are forced from the mask into the cavity 158 through the patient's air passage 160 during an inspiratory cycle. At the completion of an inspiratory cycle the patient's respiratory maintained in a blocked position by means of pilot line 130. After the initial cycle of operation the flow in line 137 will be supplemented by gases stored within the accumulator 14 which will flow through the pressure compensated check valve 148 into line 128. It should be noted that the flow through the pressure compensated check valve is made possible as the pressure in line 150 which would normally hold this valve closed is permitted to bleed through bleed to atmosphere line 154. The circuit is so designed that after the initial cycle of operation and during the inspiratory phase pressure in line 137 is less than the pressure in line 128 to insure proper operation.

At the conclusion of a normal inspiratory cycle the primary control unit 94 will cause the distributor valve 110 to be shifted against the bias of spring 112 to its expiratory position. When in this position flow from the discharge portion 50 of the pump will be directed into line 116 and past check valve 144 and into the accumulator 14. In the event that the pressure within the accumulator 14 exceeds design limits the relief vave 146 will open. In the meantime the pressure compensated check valve 148 will be hdld in its closed position by operation of the pilot line 150. During this portion of the operation the breathing gases within the patient's lungs can expire through mask 20 and the pressure compensated relief valve 142 until the desired PEEP pressure is achieved, which pressure is established by PEEP valve 118 which causes a certain pressure to be maintained within line 122 and pilot line 100.

The foregoing inspiratory and expiratory cycles will continue until the operation of the pump ceases and/or the operation of the primary control unit 94 ceases. In the embodiment illustrated the operation of both would cease at the same time since the source of pressurized breathing gases 36 is the mode of power for both the control unit 94 and the pump 32 and when the source stops putting out oxygen, normal operation will cease. At this point it is still possible to provide through manual operation the delivery of filtered breathing gases to the patient. Thus, an operator can grab the bent tube 90 and pull it away from the bottom of the housing 12 causing the accumulator 14 to expand. When this happens suction will be created in line 116 which will cause the distributor valve 110 to shift from its normal inspiratory position shown in FIG. 3 to its expiratory position against the action of spring 112 due to the operation of suction pilot line 156. Further movement of the handle 90 away from the bottom of the canister will cause air to be drawn through the filter 38 in the direction of the arrow 162 and thence through the pump 32 and valves 106 and 110 and into line 116, which gases will still be at a pressure below atmospheric thus causing the valve 110 to be maintained in its expiratory position. During this phase of operation the gases within the patient's lungs can expire through the valve 142. If the operator is trying to duplicate the normal timed cycle he will not move the handle 90 towards the bottom of the canister after the initial movement away from the canister until after completion of four seconds. At this time he will then move the handle back towards the canister forcing the filtered atmospheric gases from the accumulator 114 through line 116 and thence through pressure compensated check valve 148, branch line 128, check valve 138 and further check valve 140 and thense into the mask 20. Reverse flow through line 114 is blocked by check valve 136. The PEEP valve will continue to operate as it would during the normal mode. If the operator is trying to duplicate the normal timed cycle movement of the handle in the downward direction (FIG. 2) will preferably be done for a period of approximately two second's duration.

While in the embodiment illustrated a jet pump powered by a chlorate candle has been illustrated, it is possible to utilize other power sources or other forms of pumps. For example, it would be possible to substitute for the jet pump a centrifugal pump which could be driven either from an oxygen source or alternatively from some other source of power as for example a battery. Similarly, while the primary control unit 94 has been described as being operated by a fluidic or air logic elements, it is possible that other forms of control devices could be utilized such as for example electronic circuitry.

While a preferred structure in which the principles of the present invention have been incorporated are shown and described described above, it is to be understood that this invention is not to be limited to the particular details shown and described above, but that, in fact, widely differing means may be employed in the broader aspects of this invention.

What is claimed is:

1. A self-contained portable ventilator/resuscitator adapted to be used with a patient and being capable of operating in a normal mode during operation of a power supply to cyclically force filtered air and oxygen into the lungs of a patient and to then permit the patient's respiratory cavity to expire, said ventilator/resuscitator also being capable of being operated manually if the power supply should fail; said ventilator/resuscitator comprising:

a filter having a filter inlet open to ambient air and a filter outlet;

a power supply in the form of a source of pressurized oxygen;

pump means having a suction portion operatively interconnected with said filter outlet and a discharge portion, said pump means also being operatively interconnected to said power supply, the pump means being capable of being operated when powered by said pressurized oxygen to cause ambient air to be drawn through said filter and into said pump through said suction portion, the filtered air to be mixed with said oxygen within said pump, and the filtered air and oxygen to be discharged through said discharge portion;

outlet tubing interconnectible with said discharge portion and adapted to be connected to a patient;

an expansible and retractable accumulator, said accumulator being provided with hand engageable means which is capable of being engaged manually to cause said accumulator to be expanded or retracted; and control means normally operatively interconnected with said pump means and said accumulator and capable during operation of said power supply of either directing filtered air and oxygen to a patient and not to said accumulator during an inspiratory mode or of directing the filtered air and oxygen to said accumulator and not to the patient during an expiratory mode, and further being capable, when the power supply is not in operation, of permitting the accumulator to be manually operated to draw ambient air through the filter and into the accumulator when the accumulator is being manually expanded and to permit the filtered air in the accumulator to be forced into a patient when the accumulator is being manually retracted.

2. The self-contained portable ventilator/resuscitator as set forth in claim 1 wherein the control means is interconnected with the source of pressurized oxygen and is caused to be operated thereby.

3. The self-contained portable ventilator/resuscitator as set forth in claim 1 further characterized by the provision of a portable housing and wherein said filter and the source of pressurized oxygen are disposed in generally cylindrical containers, which containers are disposed in side-by-side relationship within said housing, said pump means and said control means also being disposed within said housing, and said accumulator being disposed to one side of said housing.

4. The self-contained portable ventilator/resuscitator as set forth in claim 3 wherein the housing is provided with clothes clips capable of securing the housing to the clothing of a patient.

5. The self-contained portable ventilator/resuscitator as set forth in claim 1 in which said pump means is a jet pump, said pressurized oxygen normally passing through a nozzle within said jet pump.

6. The self-contained portable ventilator/resuscitator as set forth in claim 5 further characterized by the provision of a portable housing and wherein said filter and the source of pressurized oxygen are disposed in generally cylindrical containers, which containers are disposed in side-by-side relationship with said housing, the outlet end of said filter container being connected in fluid tight relationship with the suction portion of said jet pump, there further being provided tubing means within said housing which extends from the source of pressurized oxygen to the nozzle of said jet pump.

7. The self-contained portable ventilator/resuscitator as set forth in claim 1 further characterized by the provision of a housing and wherein the source of pressurized oxygen, the filter the pump means, and the control means are all mounted with said housing, and said accumulator is a bellows-type accumulator mounted on one end of said housing, said accumulator further being provided with a rigid end wall remote from said housing.

8. A self-contained portable ventilator/resuscitator adapted to be used with a patient and being capable of operating in a normal mode during operation of a power supply to cyclically force filtered air and oxygen into the lungs of a patient and to then permit the patient's respiratory cavity to expire, said ventilator/resuscitator also being capable of being operated manually if the power supply should fail; said ventilator/resuscitator comprising:

a housing;

a filter mounted within said housing, said filter having a filter inlet open to ambient air and a filter outlet;

a power supply mounted within said housing, said power supply being in the form of a source of pressurized oxygen;

pump means mounted within said housing, said pump means having a suction portion operatively interconnected with said filter outlet and a discharge portion, said pump means also being operatively interconnected to said pressurized oxygen, the pump means being capable of being operated when powered by said pressurized oxygen to cause ambient air to be drawn through said filter and into said pump through said suction portion, the filtered ambient air to be mixed with said oxygen within the pump, and the filtered air and oxygen to be discharged through said discharge portion;

an expansible and retractable bellows-type accumulator mounted on one end of said housing, said accumulator being provided with a rigid end wall remote from said housing and hand engageable means in the form of a right angle tube which is capable of being engaged manually to cause said accumulator to be expanded or retracted, said right angle tube being rigidly secured to said end wall of the accumulator;

outlet tubing interconnectable to a patient, said outlet tubing including an extensible and retractable tube disposed within the accumulator and the passageway through said right angle tube; and control means mounted within said housing, said control means being operatively interconnected with said pump means, said outlet tubing, and said accumulator and capable during operation of said power supply of either directing filtered air and oxygen to a patient and not to said accumulator during an inspiratory mode or of directing the filtered air and oxygen to said accumulator and not to the patient during an expiratory mode, and further being capable, when the power supply is not in operation, of permitting said accumulator to be manually operated to draw ambient air through the filter and into the accumulator when the accumulator is being manually expanded and to permit the filtered air in the accumulator to be forced into a patient when the accumulator is being manually retracted.

9. The self-contained portable ventilator/resuscitator as set forth in claim 8 wherein said pump means is a Venturi pump having a nozzle portion interconnected with the source of pressurized oxygen.

10. The self-contained portable ventilator/resuscitator as set forth in claim 9 wherein said housing is provided with clothes clips capable of securing the housing to the clothing of a patient.

* * * * *

UNITED STATES PATENT AND TRADEMARK OFFICE
CERTIFICATE OF CORRECTION

PATENT NO. : 4,506,667
DATED : March 26, 1985
INVENTOR(S) : William K. Ansite

It is certified that error appears in the above-identified patent and that said Letters Patent are hereby corrected as shown below:

On the title page, insert the Assignee as being --Figgie International Inc.

Willoughby, Ohio--.

Signed and Sealed this

Fifth Day of November 1985

[SEAL]

Attest:

Attesting Officer

DONALD J. QUIGG

Commissioner of Patents and Trademarks